(12) United States Patent
Lieberman et al.

(10) Patent No.: US 8,066,748 B2
(45) Date of Patent: Nov. 29, 2011

(54) APPARATUS AND METHOD FOR AFFIXING BODY STRUCTURES

(75) Inventors: Isador H. Lieberman, Fort Lauderdale, FL (US); Selvon St. Clair, Cleveland Heights, OH (US); Krzysztof B. Siemionow, Shaker Heights, OH (US); Mark Kayanja, North Ridgeville, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 504 days.

(21) Appl. No.: 12/254,910

(22) Filed: Oct. 21, 2008

(65) Prior Publication Data
US 2009/0112269 A1   Apr. 30, 2009

Related U.S. Application Data

(60) Provisional application No. 60/982,216, filed on Oct. 24, 2007.

(51) Int. Cl.
*A61B 17/88* (2006.01)
(52) U.S. Cl. ...................................................... 606/279
(58) Field of Classification Search .................. 606/246, 606/279, 105, 86 R, 316, 315, 313; 623/17.11–17.16
See application file for complete search history.

(56) References Cited

U.S. PATENT DOCUMENTS

| | | |
|---|---|---|
| 2,381,050 A | 8/1945 | Hardinge |
| 4,959,064 A | 9/1990 | Engelhardt |
| 5,545,166 A | 8/1996 | Howland |
| 6,533,790 B1 | 3/2003 | Liu |
| 6,656,184 B1 | 12/2003 | White et al. |
| 7,175,626 B2 | 2/2007 | Neff |
| 2002/0198527 A1 | 12/2002 | Muckter |
| 2005/0010224 A1 | 1/2005 | Watkins et al. |
| 2005/0113919 A1 | 5/2005 | Cragg et al. |
| 2005/0143823 A1 | 6/2005 | Boyd et al. |
| 2005/0177167 A1 | 8/2005 | Muckter |
| 2006/0085075 A1 | 4/2006 | McLeer |
| 2006/0195099 A1 | 8/2006 | Bottlang |
| 2006/0235414 A1 | 10/2006 | Lim et al. |
| 2006/0264954 A1 | 11/2006 | Sweeney, II et al. |
| 2006/0271054 A1 | 11/2006 | Sucec et al. |
| 2007/0010819 A1 | 1/2007 | Johnstone |
| 2007/0055236 A1 | 3/2007 | Hudgins et al. |
| 2008/0033432 A1 | 2/2008 | McGraw et al. |

OTHER PUBLICATIONS

Grob et al. "Direct Pediculo-Body Fixation in Cases of Spondylolisthesis with Advanced Intervertebral Disc Degeneration", *Eur. Spine J.* (1996) 5:281-285.

*Primary Examiner* — Thomas C. Barrett
*Assistant Examiner* — Sameh Boles
(74) *Attorney, Agent, or Firm* — Tarolli, Sundheim, Covell & Tummino LLP (57) ABSTRACT

An apparatus for affixing a plurality of body structures together in a flexible manner includes a first articulated fastener having substantially rigid proximal and distal portions, longitudinally separated by a first flexible articulating portion. The first articulated fastener has a first thread direction. A second articulated fastener has substantially rigid proximal and distal portions, longitudinally separated by a second flexible articulating portion. The second articulated fastener has a second thread direction opposite the first thread direction. The first and second articulated fasteners are both adapted for insertion into each of the plurality of body structures. A method of affixing a plurality of body structures together in a flexible manner is also provided.

7 Claims, 7 Drawing Sheets

APPARATUS AND METHOD FOR AFFIXING BODY STRUCTURES

RELATED APPLICATION

This application claims priority from U.S. Provisional Patent Application Ser. No. 60/982,216, filed on Oct. 24, 2007, the subject matter of which is incorporated herein by reference.

TECHNICAL FIELD

The present invention relates to an apparatus and method for affixing a plurality of body structures together in a flexible manner and, more particularly, to an apparatus and method for inserting a plurality of articulated fasteners into adjacent vertebrae to aid in vertebral fusion and/or dynamic stabilization.

BACKGROUND OF THE INVENTION

Lower back pain is a common condition in the adult population and represents the most common cause of loss of work productivity. The aetiology of mechanical lower back pain includes a variety of conditions: 70% from lumbar strain or sprain; 10% from degenerative changes to discs and facets; 4% from herniated discs; 4% from osteoporotic compression fractures; 3% from spinal stenosis; and 1% from other causes (infection, ankylosing, spondylitis, neoplasms, etc.). When non-operative modalities fail, treatment may then require fusion for varied indications that include degenerative disc disease, spondylosis, age-related degeneration of the spine, infection, and primary or metastatic neoplasms. An estimated 350,000 spinal fusion procedures were performed in the U.S. in 2004 at an estimated cost of 1.5-2 billion dollars. Nevertheless, even with new advancement in surgical treatment options, lower back pain still remains a formidable challenge to physicians in the United States. Therefore, the surgeon's task remains to develop and utilize innovative and effective ways of either fusing a diseased spine or restoring stabilization while meeting the goals of preserving surrounding soft tissues, providing the optimum environment for surgical spine fusion, including restoration of alignment, halting of neurological progression, and amelioration of pain.

The conventional ventral mini-open retroperitoneal approach to the lower lumbar spine requires an initial incision usually less than ten centimeters in length and is normally employed for ventral L4-5 and L5-S1 fusion. This procedure involves dissection through the skin, soft tissue, and the rectus abdominus muscle for access into the retroperitoneal space to expose the ventral lumbar spine. A number of anatomic structures may be injured during this dissection: the ureter; the common iliac arteries and veins and the median sacral vessels. Also, damage to the presacral plexus may result in premature ejaculation in males.

A conventional ventrolateral transpsoas approach has been developed for instrumentation of L1 through L5. With the patient positioned in a 90° lateral decubitus position, the spine is accessed laterally through the psoas muscle. Through this ventrolateral approach, morbidity from dorsal or ventral exposures is limited, yet potentially still present. Furthermore, injury to the femoral or genito-femoral nerves may occur.

A conventional dorsal approach to the lumbar spine places the patient in a prone position and, through a midline 436 incision over the level of interest, dissects and laterally retracts the dorsal paraspinal muscles. Apart from a significant risk of blood loss, the dural sac, the traversing nerves and the surrounding soft tissue structures, which lie between the transverse processes lateral to the pars interarticularis and the facet joint capsules, may be injured. Peri-operative pain and post-operative scarring are typically encountered following the dorsal approach.

Spinal fusion may be performed without or without a concomitant diskectomy, and the spine may or may not be instrumented. A particular technique used to effect spinal fusion relies both on the pathology in question and the expertise of the surgeon performing the procedure. The conventional gold standard for lumbar segmental spinal fixation is a ventral interbody graft with dorsal pedicle screws. Other conventional forms of fixation include ventral plates/rods with screws and dorsal transfacet fixation.

The vast majority of the approach-related morbidity associated with open instrumented lumbar fusion procedures is caused by extensive soft tissue muscle dissection and prolonged retraction of the soft tissues and muscle. Limited retraction and exposure has been related to improved clinical outcomes with less post-operative pain. Therefore, procedures of shorter duration involving minimal dissection and retraction are desirable.

Minimally invasive approaches to lumbar spine fixation may advantageously produce decreased morbidity, limited postoperative in-patient stay, decreased cost, and the potential to improve long-term outcomes. Improved forms of instrumentation have been developed to take advantage of various access corridors to the spine, such as percutaneous introduction of pedicle screws and rods. Development of minimally invasive ventral access corridors to the lumbar spine has lagged behind dorsal access. Expandable tube retractors to allow direct visualization have been developed to assist surgeons. Navigation systems also may serve as aids for the accurate placement of pedicle screws.

Further advances in minimally invasive lumbar fixation may involve the development of a segmental lumbar fusion technique that, when used alone, eliminates the need for dorsal incisions. This technique is only available for the L5-S1 spine segment.

Minimally invasive techniques (to manage pathologic conditions in various surgical disciplines) may be successfully and reliably performed. Although the treatment of lumbar disc diseases via minimally invasive approaches is rapidly gaining acceptance, minimally invasive lumbar fusion procedures have only recently been developed and implemented. For example, a conventional axial lumbar interbody fusion/fixation uses a percutaneous pre-sacral approach for safely and effectively fusing the L5-S1 vertebral segment. There is therefore a need in the art for an improved spinal fixation apparatus and method that utilizes a minimally invasive approach with the inherent advantage of reduction in approach-related morbidity associated with conventional lumbar fusion.

SUMMARY OF THE INVENTION

In an embodiment of the present invention, an apparatus for affixing a plurality of body structures together in a flexible manner is described. A first articulated fastener has substantially rigid proximal and distal portions, longitudinally separated by a first flexible articulating portion. The first articulated fastener has a first thread direction. A second articulated fastener has substantially rigid proximal and distal portions, longitudinally separated by a second flexible articulating portion. The second articulated fastener has a second thread direction opposite the first thread direction. The first and second articulated fasteners are both adapted for insertion into each of the plurality of body structures.

In an embodiment of the present invention, an apparatus for affixing a plurality of body structures together in a flexible manner is described. A first articulated fastener has substantially rigid proximal and distal portions, longitudinally separated by a first flexible articulating portion. A second articulated fastener has substantially rigid proximal and distal portions, longitudinally separated by a second flexible articulating portion. The first and second articulated fasteners are both adapted for insertion into each of the plurality of body structures with the first and second articulating portions both at least partially located between the body structures.

In an embodiment of the present invention, a method of affixing a plurality of body structures together in a flexible manner is described. A first articulated fastener having substantially rigid proximal and distal portions, longitudinally separated by a first flexible articulating, portion, is provided. A second articulated fastener having substantially rigid proximal and distal portions, longitudinally separated by a second flexible articulating portion, is provided. The first articulated fastener is inserted into the plurality of body structures. The second articulated fastener is inserted into the plurality of body structures. The first articulated fastener is secured to at least one of the plurality of body structures by rotating the first articulated fastener in a first rotation direction. The second articulated fastener is secured to at least one of the plurality of body structures by rotating the second articulated fastener in a second rotation direction opposite the first rotation direction.

BRIEF DESCRIPTION OF THE DRAWINGS

For a better understanding of the invention, reference may be made to the accompanying drawings, in which.

DESCRIPTION OF EMBODIMENTS

Figure 1:
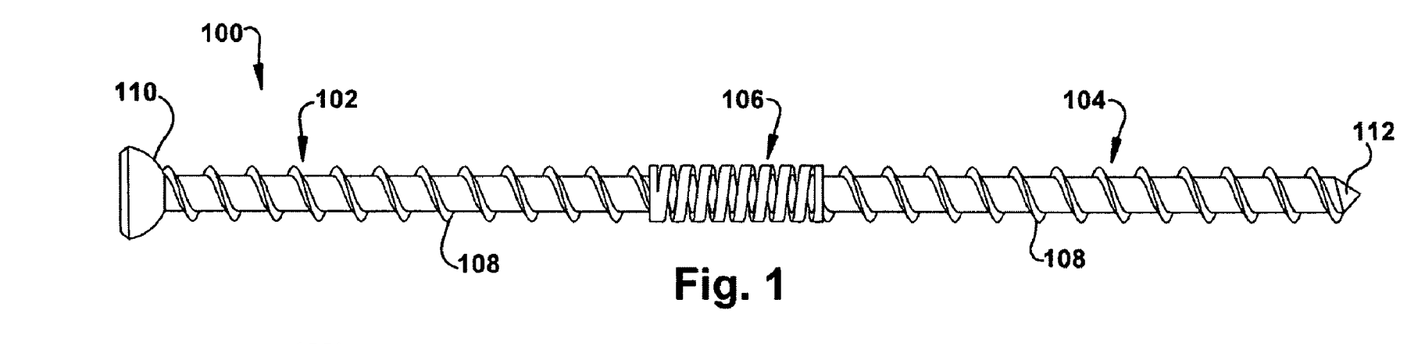
FIG. 1 is a side view of a component of a first embodiment of the present invention in a first configuration.

As depicted in FIG. 1, a first embodiment of an articulated fastener 100 in a first configuration includes substantially rigid proximal and distal portions 102 and 104, longitudinally separated by a flexible articulating portion 106. The articulated fastener 100 may be integrally formed or may be assembled from separate components. In the latter case, the separate components may be attached together in any suitable manner, and one of ordinary skill in the art can readily provide for mutual securement of the components as desired. The articulating portion 106 is shown in FIG. 1 and described herein as being a helical spring, but may have any desired form.

The articulated fastener 100, like all structures of the present invention, could be made of any suitable material and in any manner, as desired. For example, the articulating portion 106 could be made flexible by a solid or at least partially hollow elastomeric insert, a spring of any desired type, a series of relief cuts in the material forming an integral articulated fastener, any other substantially flexible component or combination thereof, or the like. The proximal and distal portions 102 and 104 could be made of any suitable material or combination of materials, such as, but not limited to, stainless steel or titanium.

The proximal and distal portions 102 and 104 may be, but are not necessarily, similar in size, shape, configuration, material, or any other property. For example, both the proximal and distal portions 102 and 104 shown in the first configuration of FIG. 1 are matched in diameter. As another example, and not shown, the articulating fastener 100 may have two diameters: a larger diameter to assist with engagement distally in the inferior vertebra 414 (pedicle and vertebral body), and a smaller diameter to assist with engagement proximally in the superior vertebra 416, with the diameters interlocking concentrically. The range of diameters may be varied to allow for different pedicle sizes.

Additionally, both the proximal and distal portions 102 and 104 are depicted as including a raised or protruding thread 108 to aid in advancing and retaining the articulated fastener 100 in a fixed relationship to another structure. Though the thread 108 is shown in FIG. 1 as extending substantially along a length of the proximal and distal portions 102 and 104 in a regular manner, the thread 108 (when present) may extend partially or wholly along either or both of the proximal and distal portions; and may vary in pitch, thread family, depth, handedness, or any other properties, either between the proximal portion and the distal portion or at different points along the same proximal or distal portion. Though a standard thread 108 and shaft arrangement is shown in FIG. 1, either or both of the proximal and distal portions 102 and 104 could instead be threaded in a "corkscrew" manner, with a single, pair, or any suitable number of spiraling spikes. Similarly a twisted rod or any other spiral or helical structure, or any combination thereof, could operate similarly to, and be substituted for, the depicted thread 108 by one of ordinary skill in the art.

It is intuitively obvious that the handedness of the thread 108, when present, should coordinate with the handedness of any spring used in the articulating portion 106 so that the spring doesn't "unscrew" and expand or splay apart under a rotational force applied to the articulated fastener 100, instead of transmitting the force from the proximal portion 102 to the distal portion 104.

Likewise, the articulating portion 106 should be designed to transmit a desired amount of rotational force between the proximal and distal portions 102 and 104. For example, the articulating portion 106 may have a stiffness chosen to help drive the distal portion 104 into bone having a particular density. The stiffness of the articulating portion 106 could also or instead be chosen to help avoid the distal portion 104 from penetrating too far into another body structure. In such case, the articulating portion 106 could act in a "circuit breaker" manner to buckle or yield (plastically and/or elastically) and substantially stop transmitting force to the distal portion 104 from the proximal portion 102 when a predetermined yield force is reached.

Optionally, a head portion 110 may be provided on the proximal portion 102 of the articulated fastener 100, to assist in engaging the articulated fastener with another structure as desired. The head portion 110, when present, may include an aperture, void, protrusion, or other feature adapted for removable engagement with a driving tool (not shown). The head portion 110 may be of the polyaxial type (not shown) with an attached plate through which a transfacet screw can be inserted. The head portion 110 may be integrally formed with the proximal portion 102 or may be separately provided, and is optionally removable from the proximal portion 102 after installation of the articulated fastener 100. Similarly, a tip portion 112 having any desired configuration may be provided on the distal portion 104 and, when present, may enable the articulated fastener 100 to be self-tapping or self-drilling. The tip portion 112 may be blunted, to help avoid damage to adjacent vascular structures.

Figure 2:
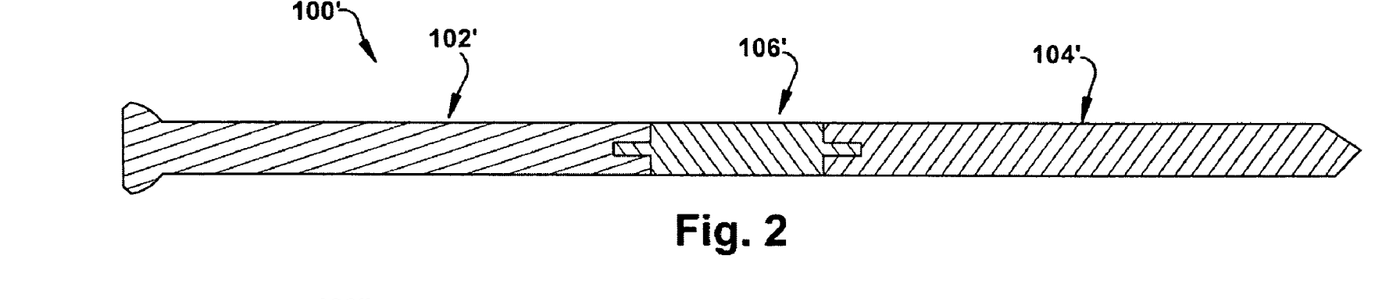
FIG. 2 is a cross-sectional view of the component of FIG. 1 in a second configuration.

FIG. 2 depicts an articulated fastener 100' in a second configuration. The articulated fastener 100' of FIG. 2 is similar to the articulated fastener 100 of FIG. 1 and therefore, structures of FIG. 2 that are the same as or similar to those described with reference to FIG. 1 have the same reference numbers with the addition of a "prime" mark. Description of common elements and operation similar to those in the previously described first configuration will not be repeated with respect to the second configuration.

In the second configuration, shown in cross-sectional view, the proximal and distal portions 102' and 104' are depicted without threads, in contrast to the first configuration. The articulated fastener 100' of FIG. 2 may be operated similarly to a known surgical spike or nail. The second configuration of the articulated fastener 100' also differs from the first configuration in the structure of the articulating portion 106'. The articulating portion 106' of the second configuration is a solid elastomeric component, which may be molded into engagement with the proximal and distal portions 102' and 104', separately formed and attached, or otherwise assembled into the articulated fastener 100' in any desirable manner.

Figure 3:
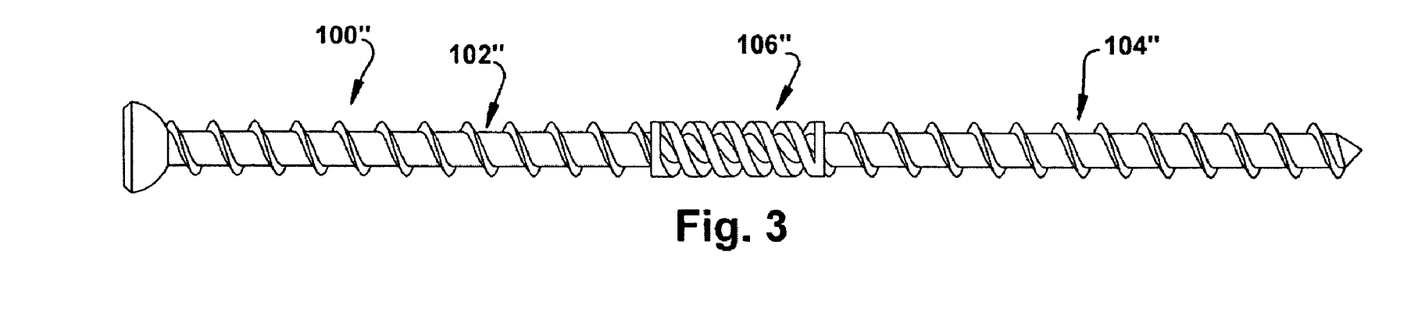
FIG. 3 is a side view of the component of FIG. 1 in a third configuration.

FIG. 3 depicts an articulated fastener 100" in a third configuration. The articulated fastener 100" of FIG. 3 is similar to the articulated fasteners 100 and 100' of FIGS. 1 and 2, respectively, and therefore, structures of FIG. 3 that are the same as or similar to those described with reference to FIGS. 1 and 2 have the same reference numbers with the addition of a double "prime" mark. Description of common elements and operation similar to those in the previously described first and second configurations will not be repeated with respect to the third configuration.

In the third configuration, shown in side view, the proximal and distal portions 102" and 104" are depicted with threads, like the first configuration. However, the third configuration of the articulated fastener 100" also differs from the first and second configurations in the structure of the articulating portion 106". The articulating portion 106" of the third configuration is a double helix of spiraling spikes, which may be formed integrally with the proximal and distal portions 102" and 104", separately formed and attached, or otherwise assembled into the articulated fastener 100" in any desirable manner.

The articulated fasteners 100, 100', and 100" depicted in FIGS. 1, 2, and 3 are merely examples of a wide range of articulated fasteners, having many different combinations of structures, which could be used with the method of the present invention. In general, a suitable articulated fastener, regardless of its particular configuration, can be readily provided by one of ordinary skill in the art for use with the inventive method for affixing a plurality of body structures together in a flexible manner.

When applied to body structures, the term "flexible" is used herein to indicate a secure connection that nonetheless allows a small degree of relative movement between the structures. For example, when two bones are affixed together by an articulated fastener, adjacent musculature may apply forces to the bones. In some applications of the present invention, a completely rigid affixation might result in bone fractures due to these applied forces. Since bones themselves are tolerant of a small degree of deformation, a "flexible" connection may be chosen to permit at least a similar degree of deformation, or any other degree of deformation as desired for a particular application of the present invention. Two body structures affixed in a "flexible" manner nonetheless are still constrained or restricted in their relative movement, to some degree, by the affixation means.

Regardless of the degree of elasticity/deformation chosen for the flexible connection between the body structures, a method in accordance with the present invention may be used, for example, to provide a minimally invasive and reliable placement of spinal fusion implants between two or more adjacent vertebrae to facilitate mutual affixation of those vertebrae. The method may be percutaneously applied to interbody vertebral fixation at a desired location, discussed here as being at or above the L5-S1 vertebral segment. The method can be performed as an outpatient procedure for vertebral body fixation and therefore may cost less than conventional invasive surgical approaches, which normally require at least three to five days' stay in the hospital.

Figure 4:
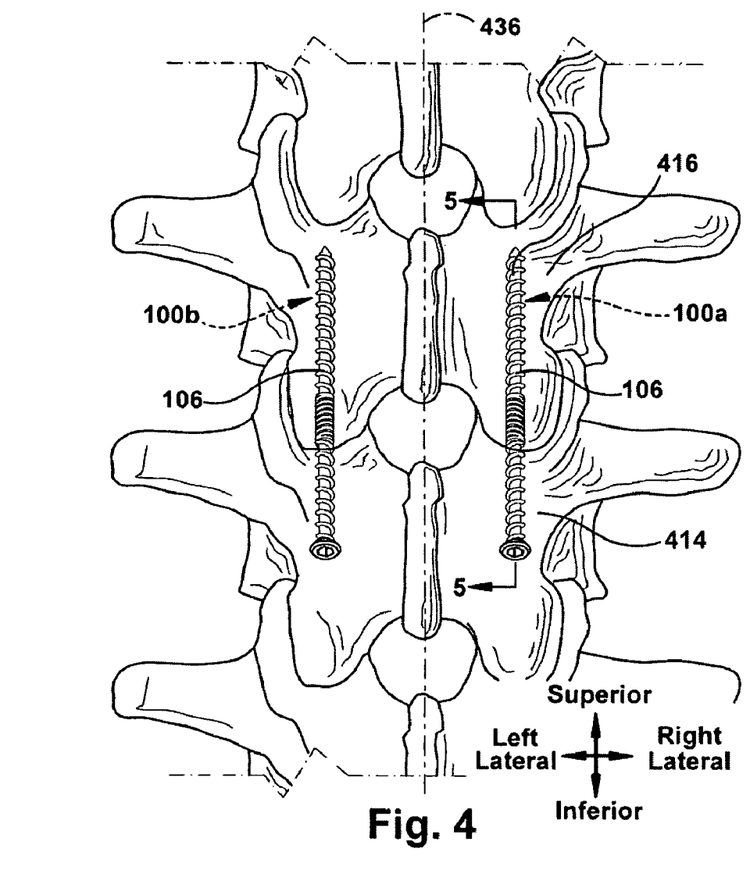
FIG. 4 is a partial posterior view of a first example use environment of the component of FIG. 1.
Figure 5:
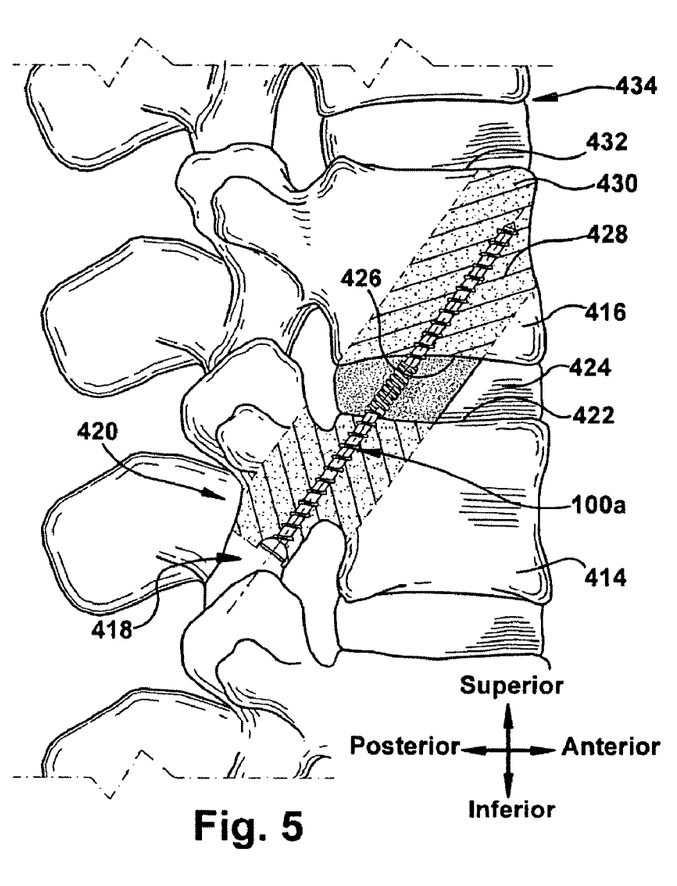
FIG. 5 is a partial cross-sectional right lateral view, taken along line 5-5 of FIG. 4.

As shown in FIGS. 4 and 5, the method comprises percutaneous lumbar interbody screw fixation of two articulated fasteners 100 for use in a first example application. In this first example application, the articulated fasteners 100 are inserted into adjacent inferior and superior vertebrae, 414 and 416, respectively, which will be presumed in the below description to be lumbar vertebrae. This insertion may follow a diskectomy, also performed with percutaneous tools, through a lateral extraforaminal approach. After the diskectomy, an interbody craft placement and screw insertion may be performed using the inventive method. As shown in FIG. 5, the trajectory of the articulated fasteners 100 extends from the inferior articular process 418 of the facet joint of the inferior vertebra 414; traversing the pedicle 420 of the inferior vertebra; through the superior endplate 422 of the inferior vertebra; across the interbody space 424 between the inferior and superior vertebrae 414 and 416; through the inferior endplate 426 of the superior vertebra 416; through the centrum 428 of the superior vertebra; and toward the junction 430 of the superior endplate 432 with the anterior vertebral surface (generally shown at 434) of the superior vertebra.

The method provides for rigid interbody vertebral fixation via a percutaneous approach. This method uses an articulated fastener 100 device and delivery system as a stand-alone device or in combination with anterior lumbar interbody fusion to facilitate a stable fusion between vertebrae segments. The method further provides for percutaneous intervertebral disc removal prior to a fusion procedure or for a diagnostic biopsy. The method also provides percutaneous preparation and fixation of facet joints for fusion. The method includes percutaneous screw insertion with two articulated fasteners 100 inserted obliquely through two adjacent vertebrae 414, 416. As shown in FIG. 5, the articulated fasteners 100 extend in an inclined, or slanted, manner such that the articulated fasteners are angled from the posterior direction toward the anterior direction while extending between the superior and anterior directions. The articulating portions 106 of the articulated fasteners 100 should be located at least partially in the interbody space 424, whether or not an intervertebral disk is also present in that area, to provide the desired flexible affixation. Though the articulated fasteners 100 are depicted in the Figures as having substantially similar orientations when implanted, one of ordinary skill in the art can readily determine desired angles of implantation, which may be similar or different to one another, for each of the articulated fasteners in a particular application of the present invention.

The method provides a completely percutaneous and rodless oblique interbody fixation system which may be used, for example, to transfix lumbar vertebrae segments at and above the L5-S1 level. The method precisely defines a screw trajectory, using fluoroscopy or another imaging technique before or during surgery, for the oblique insertion of guide wire-assisted articulated fasteners 100 across an interbody joint. The articulated fasteners 100 traverse the pedicle 420 of the inferior vertebra 414, the interbody space 424, the inferior endplate 426, and centrum 428 of the superior vertebra 416, and terminate at the junction 430 of the superior endplate 432 and anterior vertebral surface 434 of the superior vertebra. The method also may be used to further apply facet fixation mapping using similar techniques.

One example of a specific surgical procedure using the present method will now be described. The method employs a dorsal approach (from posterior to anterior) to the spine with the patient in the prone position. The level of approach is confirmed with anteroposterior and lateral fluoroscopy. The midline 436, as seen in FIG. 4, is identified and marked, e.g., with an indelible marker. Paramedian lines (not shown), for guiding insertion of the articulated fasteners 100, are then drawn on the skin at chosen locations, such as, for example, four to five centimeters offset from the midline 436. These paramedian lines may be, but are not necessarily, symmetrical about the midline 436. Under lateral fluoroscopy, a spinal needle, such as a 22-gauge needle, is inserted along one of the paramedian lines and advanced until its trajectory bisects an inferior junction of the inferior pedicle 420 and inferior articular process 418. Antero-posterior fluoroscopy (not shown) may be used to confirm the medial-lateral position of the needle that should be positioned to engage the lateral cortical rim of the pedicle 420 at this point in the procedure.

Under fluoroscopic guidance, the spinal needle is next obliquely advanced through bone into the pedicle 420 in a direction from inferior to superior. It may be desirable to obtain sequential, biplanar fluoroscopic images to guide the tip of the needle to a desired distance, such as, for example, four to five millimeters from the junction 430 of the superior endplate 432 and anterior vertebral surface 434. Eventual K-wire placement is provided such that the medial pedicle 420 wall, and the anterior edge of the superior endplate 432 of the same vertebra, are not breached as may be determined or confirmed by antero-posterior fluoroscopy. A K-wire is then placed through the needle, which may subsequently be removed. The K-wire is then advanced under lateral fluoroscopic guidance through the disc and inferior endplate 426 of the superior vertebra 416 to a desired position, such as, for example, four to five millimeters from the ipsilateral junction 430 of the superior endplate 432 and the anterior vertebral surface 434.

Antero-posterior fluoroscopy or other imaging means then may be used to confirm the medial-lateral position of the oblique interbody vertebral fixation and establish a desired screw trajectory. When imaging reveals that the K-wire is not in position as desired, the above process, or portions thereof, may be repeated until the K-wire achieves the desired positioning. Alternatively, in lieu of the initial 20 guage spinal needle, the above process may be performed with at least one of a smooth K-wire, a threaded K-wire, a Jamshidi needle, a combination pin/drill, or the like, which may be utilized, for example, under fluoroscopic guidance or robotic/navigation guidance Once the desired superior-anterior trajectory for insertion of the articulated fastener 100 is established, in the above or any other suitable manner, skin incisions may be made as appropriate, aided, if desired, by fluoroscopic or other imaging tools. Next, a trocar and/or cannula may be inserted to open the soft tissues for insertion of the articulated fastener 100. A Jamshidi needle may then be docked on the spine at the appropriate location (for example, at the L2 for L1-2, the L3 for L2-3, the L4 for L3-4, the L5 for L4-5, or the S1 for L5-S1) and the trajectory adjusted, under fluoroscopy, to ensure entry at the inferior junction of the pedicle 420 and inferior articular process 418, and termination at the junction 430 between the anterior vertebral surface 434 and the superior endplate 432. The cortex is opened to make way for the K-wire, which is then inserted along the previously mapped/planned oblique interbody screw trajectory. Using standard equipment and fluoroscopy, the K-wire is advanced under lateral fluoroscopic guidance from the inferior junction of the inferior pedicle 420 and inferior articular process 418 through the intervertebral disc, inferior endplate 426 of the superior vertebra 416, stopping just short of the junction 430 of the superior endplate 432 and anterior vertebral surface 434.

Once the K-wire is positioned, the trajectory hole may be tapped and/or drilled as needed. This is followed by implantation of the articulated fastener 100. The articulated fastener 100 may also or instead be cannulated to accommodate a guide wire for implantation.

Antero-posterior fluoroscopy or another imaging means may be used to confirm the medial-lateral position of the inserted articulated fastener 100. The articulated fastener 100, in final position following the above steps, traverses the pedicle 420 of the inferior vertebra 414, the interbody space 424, the inferior endplate 426 and centrum 428 of the superior vertebra 416, and terminates at the junction 430 of the superior endplate 432 and anterior vertebral surface 434 of the superior vertebra, as shown in FIGS. 4 and 5. A second articulated fastener 100 may be inserted, in parallel or in series, to the first articulated fastener 100 as described above, using similar steps.

In the first example use environment of FIGS. 4 and 5, the articulated fasteners 100 depicted are not identical. Instead, the right articulated fastener 100a is right-hand threaded, for insertion through clockwise rotation, as is standard in the United States for screw threads. In contrast, the left articulated fastener 100b is left-hand threaded, for insertion through counterclockwise rotation. This opposite threading between the two articulated fasteners 100a and 100b may help to better balance the insertion and retention forces applied to the inferior and superior vertebrae 414 and 416 than if both the articulated fasteners 100a and 100b were threaded in the same direction.

Figure 6:
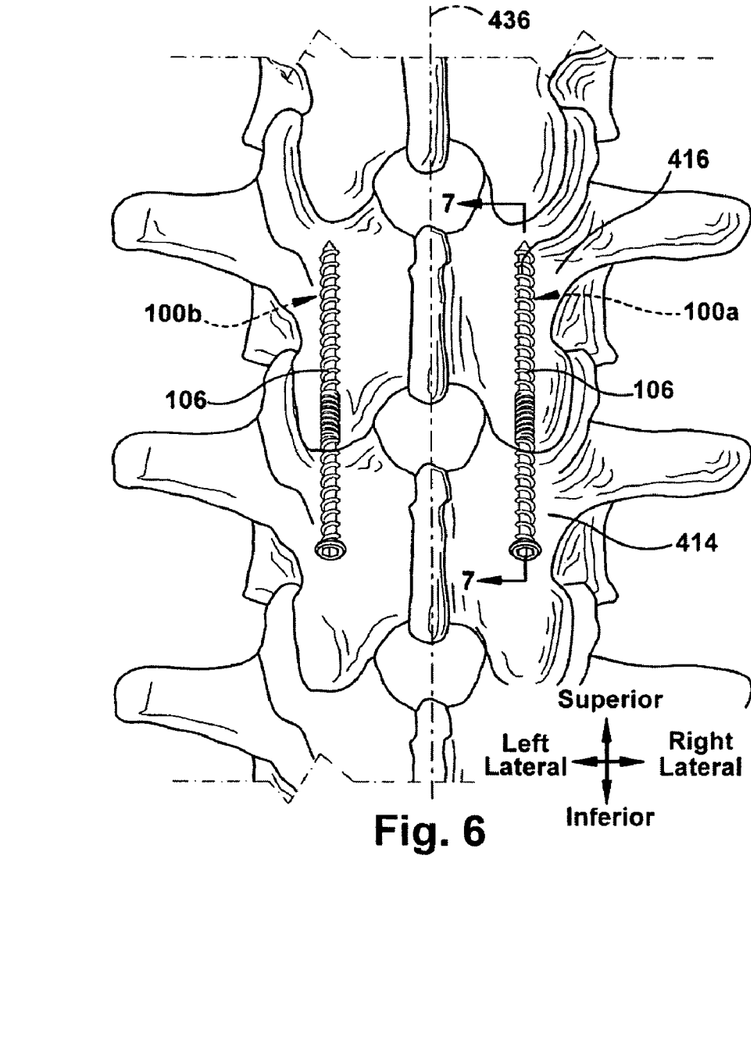
FIG. 6 is a partial posterior view of a second example use environment of the component of FIG. 1.
Figure 7:
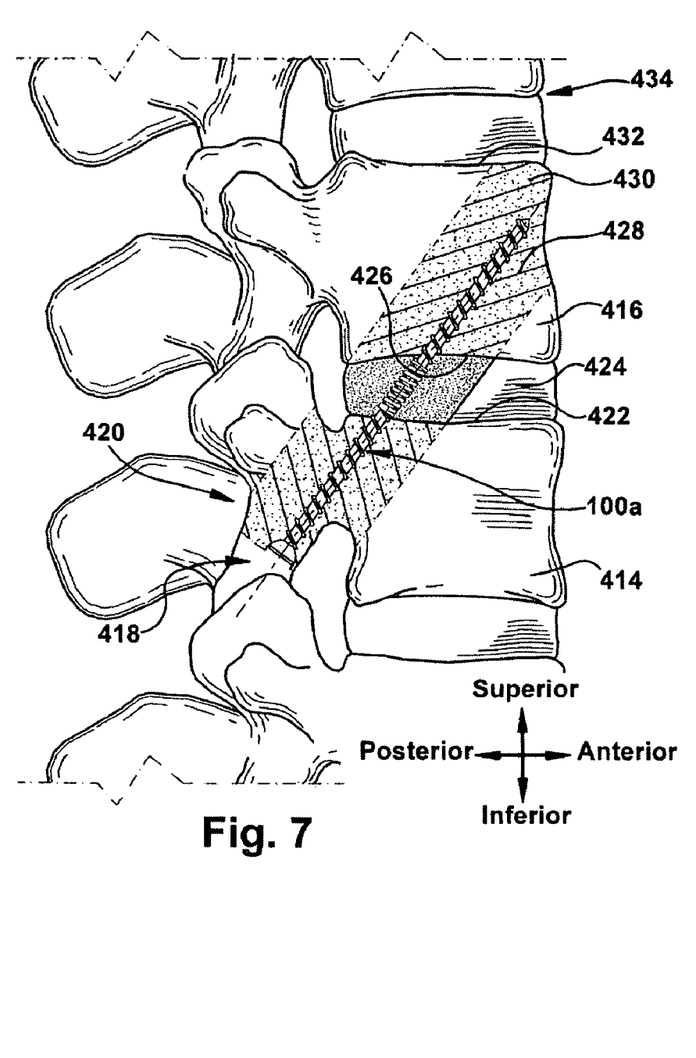
FIG. 7 is a partial cross-sectional right lateral view, taken along line 7-7 of FIG. 6.

Likewise, and as shown in the second example use environment of FIGS. 6 and 7, the two articulated fasteners 100a and 100b could be positioned contralaterally to the first example use environment. In FIGS. 6 and 7, the right-hand threaded articulated fastener 100a is on the left side of the midline 436, and the left-hand threaded articulated fastener 100b is on the right side of the midline 436. This alternate arrangement of the articulated fasteners 100a and 100b may result in different forces being applied to the inferior and superior vertebrae 414 and 416 than in the first example use environment, above. Though the articulated fasteners 100a and 100b may have any desired relative positioning, the following description will presume that the articulated fasteners 100a and 100b are positioned as in the first example use environment, for ease of identification and reference.

Figure 8:
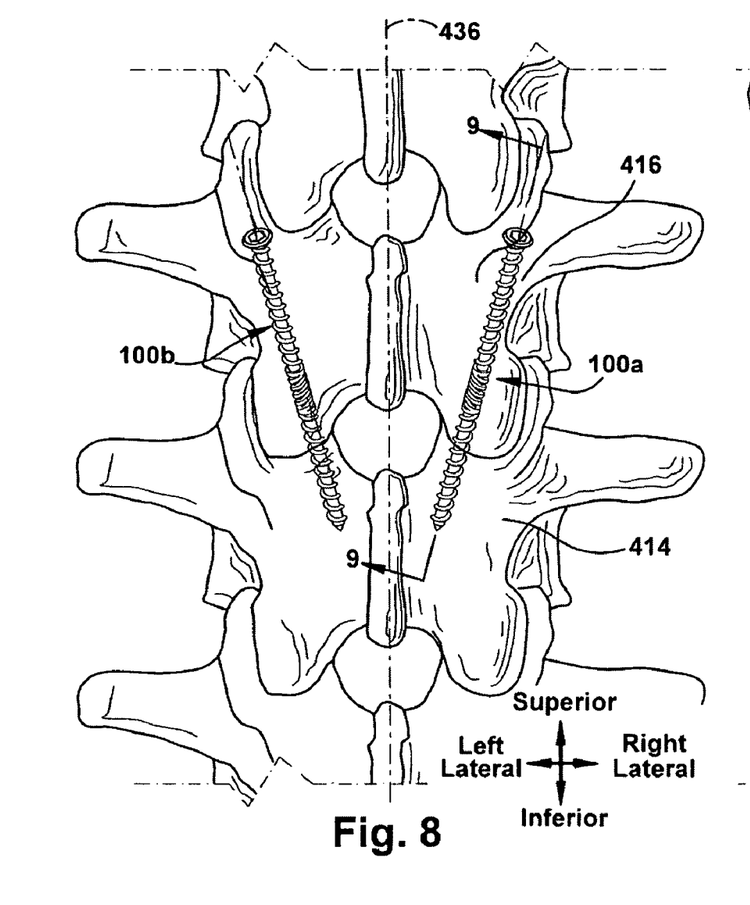
FIG. 8 is a partial posterior view of a third example use environment of the component of FIG. 1.
Figure 9:
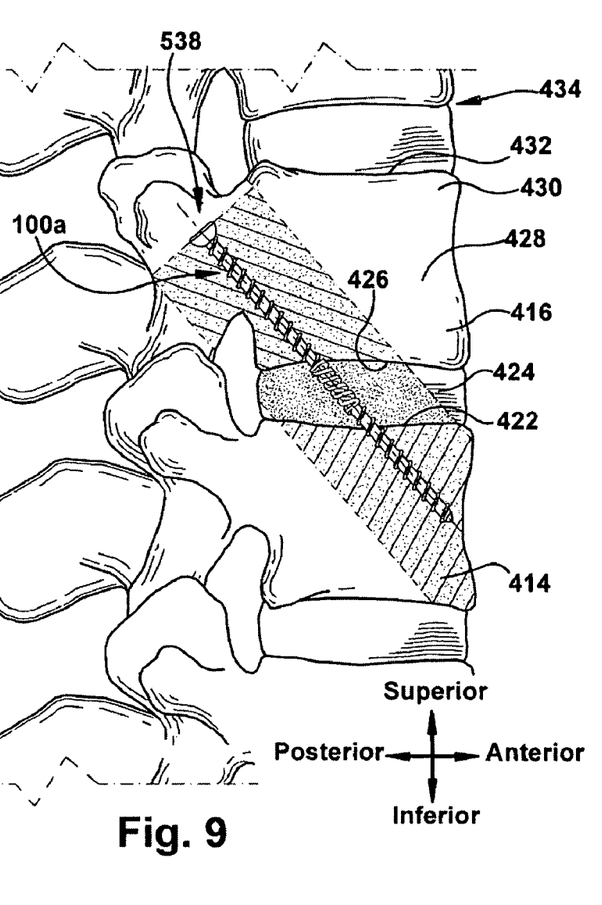
FIG. 9 is a partial cross-sectional right lateral view, taken along line 9-9 of FIG. 8.

FIGS. 8 and 9 depict a third example use environment of the articulated fasteners 100. As shown in FIG. 9, the trajectory of each articulated fastener 100 extends from the junction 538 of the superior articular process and the transverse process of the superior vertebra 416, in the inferior direction through the centrum 428 of the superior vertebra, obliquely traversing the pedicle, through the inferior endplate 426 of the superior vertebra, through the interbody space 424, and into the vertebral body of the inferior vertebra 414. In combination with this inferior-anterior trajectory, each articulated fastener 100 may be directed slightly medially (towards the midline 436), as shown in FIG. 8, towards the sagittal midpoint of the inferior vertebra 414. This medial tilt may be provided with any of the articulated fasteners 100 discussed herein, in any example use environment or another environment, not discussed.

Figure 10:
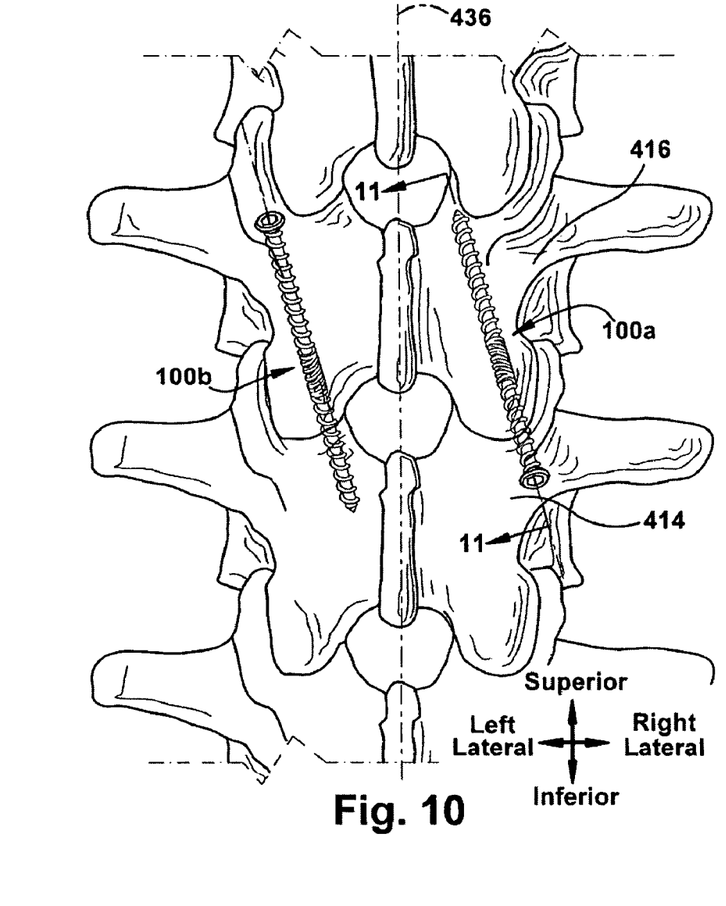
FIG. 10 is a partial posterior view of a fourth example use environment of the component of FIG. 1.
Figure 11:
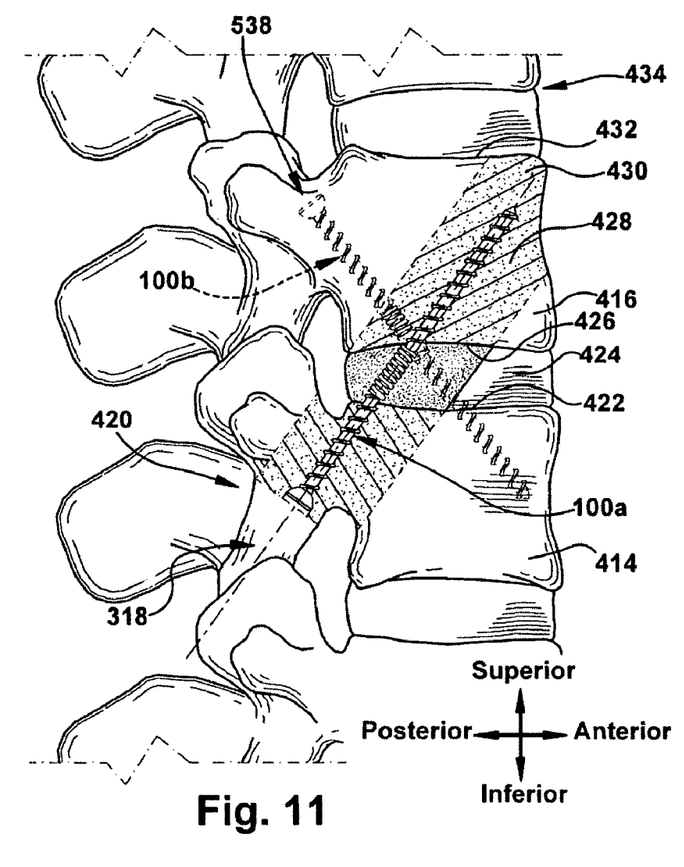
FIG. 11 is a partial cross-sectional right lateral view, taken along line 11-11 of FIG. 10.

FIGS. 10 and 11 depict a fourth example use environment of the articulated fasteners 100, which includes features of both the first/second example use environments and the third example use environment. As shown in FIGS. 10 and 11, the right-side articulated fastener 100a has a superior-anterior trajectory as described with reference to the first and second example use environments, while the left-side articulated fastener 100b has an inferior-anterior trajectory as described with reference to the third example use environment. As with all environments and embodiments described herein, the trajectories of the articulated fasteners 100a and 100b in the fourth example use environment need not exactly follow the described paths, through the same anatomical landmarks, as those previously described with respect to the first through third example use environments, as long as the same general trajectory direction (i.e., superior-anterior or inferior anterior) is maintained.

Though the depicted example use environments of the first embodiment of the present invention, depicted in FIGS. 4-11, respectively, are shown with two symmetrically articulated fasteners 100a and 100b each, any number of articulated fasteners can be used, and in any suitable positions. For example, an additional pair of articulated fasteners (not shown) could be positioned similarly to those shown, but on superiorly or inferiorly adjacent vertebrae to those currently engaged by the articulated fasteners 100. Likewise, additional articulated fasteners (not shown) could extend between the superior and inferior vertebrae 414 and 416 to supplement the flexible affixation provided by the depicted articulated fasteners. Additional articulated fasteners, when present, may have any desired placement, configuration, material, size, shape, handedness, and any other properties, and the articulated fasteners need not match each other in any respect, except as desired. One of ordinary skill in the art can readily determine the desired characteristics and properties desired for the articulated fastener(s) for a particular application of the present invention.

A transfacet insertion path method (not shown) may be used for one or both of the articulated fasteners 100 of the first embodiment, in addition to or instead of the above-described positioning. For transfacet fixation, before a surgical incision, a level of approach is confirmed with antero-posterior and lateral fluoroscopy. The midline 436 is identified and marked. Paramedian lines are then drawn at a desired position, such as, for example, four to five centimeters off midline 436. Under lateral fluoroscopy, an appropriate needle, such as an 11-gauge spinal needle (not shown), is inserted lateral and collinear to the transverse process, through the paramedian lines. The needle is advanced until its trajectory bisects the posterior junction of the superior articulating facet and the transverse process. Antero-posterior fluoroscopy then may be used to confirm a medial-lateral position of the needle that engages the lateral cortical rim of the superior articulating process.

Under fluoroscopic guidance, the spinal needle is obliquely advanced into the superior articulating process from inferior to superior until the inner cortex/cartilage border is reached. A K-wire is then placed through the needle, which is subsequently removed. The K-wire is then advanced under lateral fluoroscopic guidance through the facet joint space, cartilage/inner (lateral) cortex of the inferior articulating facet until the medial (outer) wall of that facet, without violating that cortex. Antero-posterior fluoroscopy then may be used to confirm the medial-lateral position of the intended path for collinear facet fixation.

For facet joint fixation, the K-wire is obliquely advanced, for example, at an angle which could be in the range of 45° to 55°, from the dorsal junction of the superior articular process and the transverse process into the superior articular process from inferior to superior, through the facet joint space, cartilage/inner (lateral) cortex of inferior articulating facet until the medial wall of that facet without violating this cortex. Antero-posterior fluoroscopy then confirms the medial-lateral position of the collinear facet fixation.

FIGS. 12-15 illustrate a second embodiment of an articulated fastener 1240. The articulated fastener 1240 of FIGS. 12-15 is similar to the articulated fastener 100 of FIGS. 1-11; description of common elements and operation similar to those in the previously described first embodiment will not be repeated with respect to the second embodiment.

Figure 12:
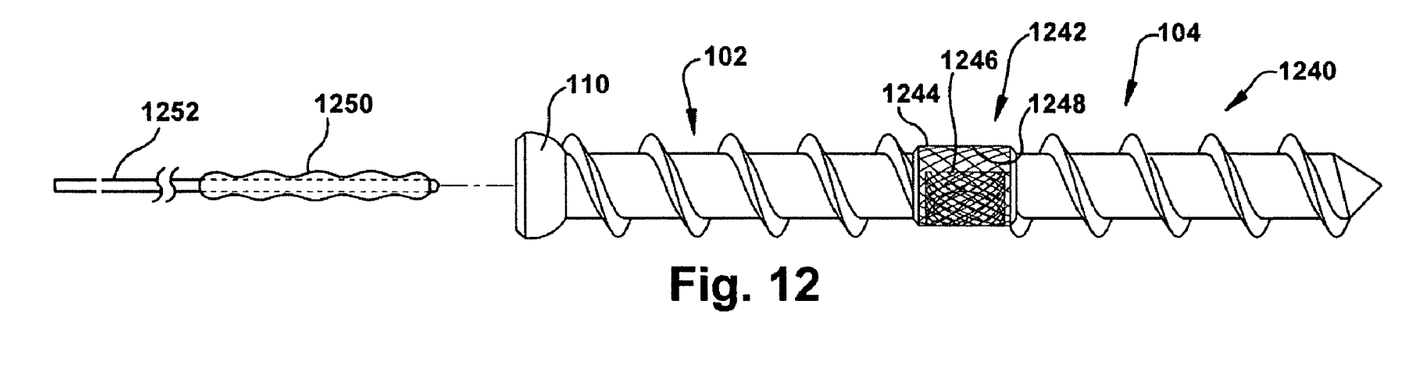
FIG. 12 is a side view of a component of a second embodiment of the present invention in a first configuration.
Figure 13:
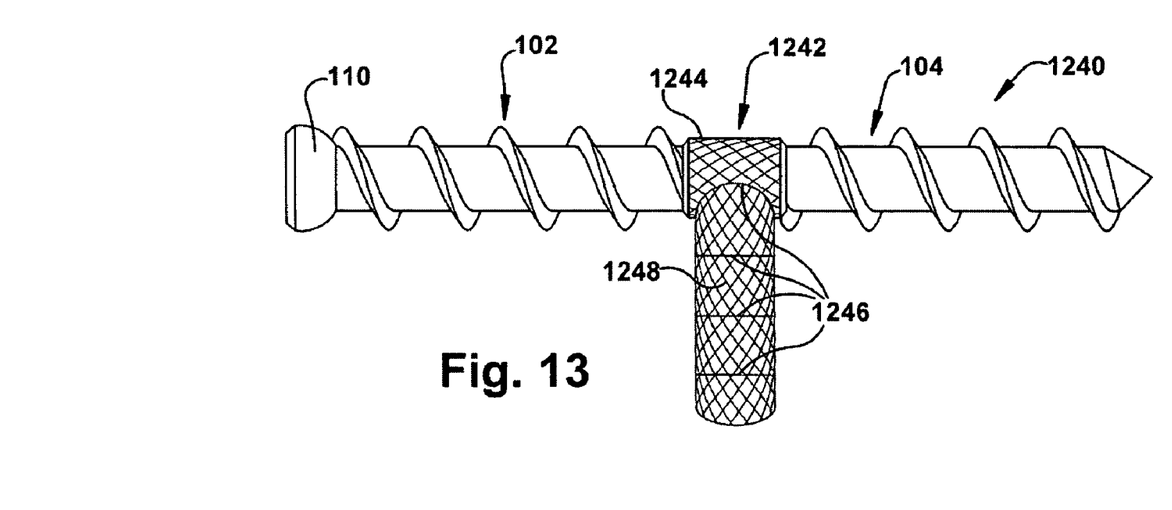
FIG. 13 is a side view of the component of FIG. 12 in a second configuration.

As shown in FIGS. 12-13, the articulated fastener 1240 includes a dual-featured articulating portion 1242. In addition to affixing a plurality of body structures together in a flexible manner, the articulating portion 1242 includes an expanding portion 1244 which is adapted to selectively laterally extend from the articulated fastener 1240. The expanding portion is adapted to at least partially occupy the interbody space 424, laterally spaced from the proximal and distal portions 102 and 104, when expanded.

The expanding portion 1244 may be made of any material, and may have any size, shape, configuration, material properties, subassemblies, other characteristics, or the like, and may readily be provided for a particular application of the present invention by one of ordinary skill in the art. For the sake of discussion, the expanding portion 1244 will be described herein as an at least partially balloon-expanded cage, having a plurality of frame members 1246 supporting a metallic mesh 1248, and is configured to fit inside the interbody space 424.

When stowed, and as shown in FIG. 12, the expanding portion 1244 may have a similar diameter to those of at least one of the adjacent proximal and distal portions 102 and 104. There is optionally a stiffening rod (not shown) or other reinforcing structure extending through at least part of the expanding portion 1244 to assist in maintaining the structure of the articulated fastener 1240 during insertion. Particularly when the articulated fastener 1240 is threaded for rotary insertion, an indication of the radial orientation of the articulated fastener (for example, a marking on the head portion 110) may be provided to facilitate deployment of the expanding portion 1244 into a desired position at least partially within the interbody space 424.

To deploy a balloon-expanded expanding portion 1244, a deflated balloon 1250 may be inserted into an implanted articulated fastener 1240 with a catheter 1252, as shown in FIG. 12. To facilitate this insertion, at least the proximal portion 102 may include a throughbore (not shown) through which the catheter 1252 may pass. Once the balloon 1250 is at least partially within the articulating portion 1242, any desired orientation adjustments may be made and the catheter 1252 may then be used to inflate the balloon 1250. As the balloon 1250 is inflated, it exerts pressure from within to deploy the expanding portion 1244 laterally from the proximal and distal portions 102 and 104, as shown in FIG. 13. The term "lateral" is used herein to indicate a direction perpendicular to the midline 436, as shown by the orientation arrows in FIGS. 4, 6, 8, 10, and 14. A "lateral" direction is optionally also "medial" (i.e., toward the midline 436). When the expanding portion 1244 has reached a desired shape, the balloon 1250 is deflated and withdrawn from the articulated fastener 1240 by the catheter 1252.

Figure 14:
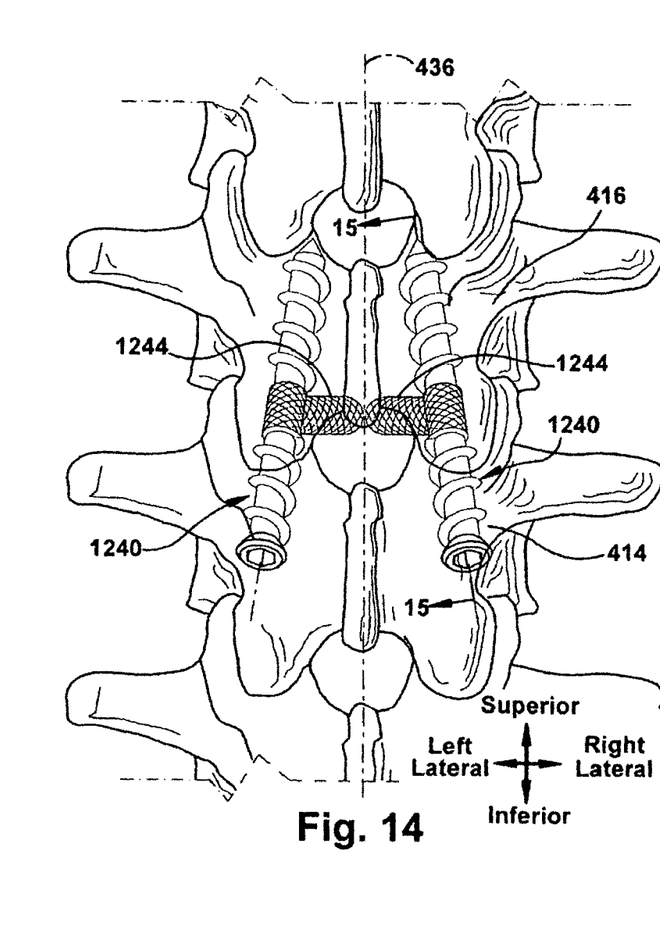
FIG. 14 is a partial posterior view of an example use environment of the component of FIG. 12.
Figure 15:
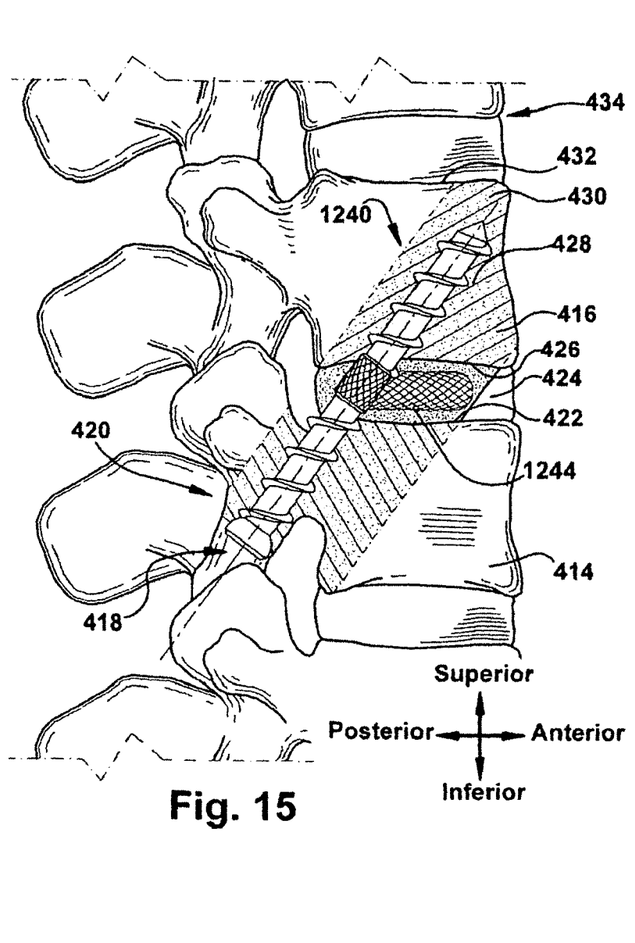
FIG. 15 is a partial cross-sectional right lateral view, taken along line 15-15 of FIG. 14.

FIGS. 14 and 15 depict an example use environment of the second embodiment of the present invention. Though two articulated fasteners 1240 are shown in these Figures as being implanted in the vertebrae 414 and 416 in a similar arrangement to the first example use environment of FIGS. 4 and 5 for ease of discussion, any suitable placement and positioning of the articulated fasteners 1240 may be used, as desired. For instance, the articulated fasteners 1240 are angled toward the midline 436, as shown in FIG. 14, than those in the previously described first example use environment. Nonetheless, the superior-anterior trajectory of the articulated fasteners 1240 is sufficiently similar to that of FIGS. 4 and 5 that the above description will not be repeated here. One of ordinary skill in the art can readily provide articulated fasteners 1240 having suitable configuration and positioning for a particular application of the present invention. For example, the articulated fasteners 1240 may be of a nail or spike type, or may have either opposite or matched threads for rotary insertion, as desired.

Once the articulated fasteners 1240 are in place, and regardless of the configuration and positioning thereof, the expanding portions 1244 may be deployed as described above or in any other suitable manner. One or both expanding portions 1244 may be used to occupy the interbody space 424 to a desired extent. When two articulated fasteners 1240, but only one expanding portion 1244, are used, the non-expanded articulated fastener may be of any desired type (for example, may be an articulated fastener 100 of the first embodiment) or may even be a standard fastener, lacking an articulating portion 106 or 1242. When a plurality of expanding portions 1244 are used, the total volume occupied within the interbody space 424 may be split in any desired proportions and need not be divided symmetrically; each expanding portion 1244 occupies about half of the total occupied volume in the example use environment of FIGS. 14 and 15. Additionally, each of a plurality of expanding portions 1244 may have expansion characteristics chosen responsive to the position of that expanding portion in the interbody space. For example, an expanding portion 1244 in one area (e.g. the right lateral side) may be configured to exert more pressure on adjoining vertebrae 414 and 416 than an expanding portion in another area (e.g. the left lateral side) in order to help correct a spinal imbalance.

The expanding portion 1244 may be hollow or at least partially filled with a desired, preferably biocompatible, material. For example, the expanding portion 1244 could contain bone graft and accordingly act as a fusion cage in a vertebral fusion procedure. As another example, and particularly when the material of the expanding portion 1244 is chosen to retain another substance therein, the expanding portion could be filled with a cushioning gel or other substance to function as an artcifial intervertebral disk. The expanding portion 1244 could also or instead be adapted to elute a therapeutic agent, such as, but not limited to, an anesthetic, anti-inflammatory, or antiseptic fluid, to the interbody space 424 and/or adjacent vertebrae 414 and 416. "Elute" is used herein to indicate that a therapeutic agent is released, leached, diffused, or otherwise provided to the target tissue.

While aspects of the present invention have been particularly shown and described with reference to the preferred embodiments above, it will be understood by those of ordinary skill in the art that various additional embodiments may be contemplated without departing from the spirit and scope of the present invention. For example, the articulated fasteners 100 could be used to connect a plurality of any bones or other body structures while allowing for a limited amount of movement therebetween. The specific method described above for inserting the articulated fasteners 100 is merely illustrative; one of ordinary skill in the art could readily determine any number of tools, sequences of steps, or other means/options for placing the articulated fasteners into positions substantively similar to those shown and described herein. The articulated fasteners 100 could have associated therewith a removable or at least partially biodegradable rod or other stiffening member (not shown), to help the articulating portion 106 transfer forces efficiently between the proximal and distal portions 102 and 104 during installation. The articulating portion 106 may include several components to exhibit a desired degree of flexibility. When the articulated fasteners 100 are used to affix more than two body structures together, there may be more than one articulating portion 106 per articulated fasteners. Either of the above-described methods, or any other method, may be employed in conjunction with an anterior interbody fusion with bone graft, through which the articulated fastener 100 may pass. The method(s) may be performed completely percutaneously or as a mini-open approach/procedure. The method(s) may be utilized to fuse the T12/L1, L1/L2, L2/L3, L3/L4, L4/L5 and L5/S1 vertebral segments, or in any other suitable application. While certain anatomical landmarks are discussed in conjunction with the trajectories of various articulated fasteners 100 above, one of ordinary skill in the art can readily map a desired trajectory through any anatomical structures (whether or not described herein), which optionally results in similar mechanical properties in the installed articulated fastener as the described trajectories, for a particular application of the present invention. The expanding portion 1244 could be self-expanding (e.g., made from a shape memory and/or elastically deformed material), and a sheath (not shown) could be provided to the articulated fastener 1240 to contain the expanding portion 1244 before deployment. The balloon 1250 may be shaped to at least partially mimic the shape of the deployed expanding portion 1244. Any number and combination of articulated fasteners 100 and 1240, and optionally standard (non-articulated) fasteners, may be used to provide a desired affixation of the body structures. The articulated fasteners 100 and 1240 may be inserted into the body structures using any suitable tool, method, procedure, technique, or the like, following an assisting pilot hole or structure or instead making the initial penetration with no assisting structure. A device or method incorporating any of these features should be understood to fall under the scope of the present invention as determined based upon the claims below and any equivalents thereof.

By virtue of the disclosed apparatus and/or method, an articulated fastener 100 may be placed at or near the instantaneous axis of rotation of one or more vertebrae 414 and 416, to facilitate attempts to normalize motion (i.e. dynamic stability) for certain patients in a desired manner.

Other aspects, objects, and advantages of the present invention can be obtained from a study of the drawings, the disclosure, and the appended claims.

Having described the invention, we claim:

1. A method of affixing a plurality of body structures together in a flexible manner, the method comprising the steps of: providing a first articulated fastener having substantially rigid proximal and distal portions, longitudinally separated by a first flexible articulating portion; providing a second articulated fastener having substantially rigid proximal and distal portions, longitudinally separated by a second flexible articulating portion; inserting the first articulated fastener into the plurality of body structures; inserting the second articulated fastener into the plurality of body structures; securing the first articulated fastener to at least one of the plurality of body structures by rotating the first articulated fastener in a first rotation direction; and securing the second articulated fastener to at least one of the plurality of body structures by rotating the second articulated fastener in a second rotation direction opposite the first rotation direction, wherein the step of inserting the first articulated fastener into the plurality of body structures includes the step of inserting the first articulated fastener into a plurality of adjacent vertebrae, and the step of inserting the second articulated fastener into the plurality of body structures includes the step of inserting the second articulated fastener into a plurality of adjacent vertebrae.

2. The method of claim 1, including the steps of:
positioning the first articulated fastener in relation to the plurality of body structures with the first articulating portion at least partially located between adjacent body structures; and
positioning the second articulated fastener in relation to the plurality of body structures with the second articulating portion at least partially located between adjacent body structures.

3. The method of claim 1, wherein the step of inserting the first articulated fastener into a plurality of adjacent vertebrae includes the step of extending the first articulated fastener from a pedicle of an inferior vertebra, through an interbody space, through an inferior endplate and centrum of a superior vertebra, and to a junction of a superior endplate and an anterior vertebral surface of the superior vertebra; and
the step of inserting the second articulated fastener into a plurality of adjacent vertebrae includes the step of extending the second articulated fastener from a pedicle of an inferior vertebra, through an interbody space, through an inferior endplate and centrum of a superior vertebra, and to a junction of a superior endplate and an anterior vertebral surface of the superior vertebra.

4. The method of claim 1, wherein the step of inserting the first articulated fastener into a plurality of adjacent vertebrae includes the step of extending the first articulated fastener from a junction of a superior articular process and a transverse process of a superior vertebra, in an inferior direction through a centrum of the superior vertebra, obliquely traversing a pedicle, through an inferior endplate of the superior vertebra, through an interbody space, and into a vertebral body of an inferior vertebra; and
the step of inserting the second articulated fastener into a plurality of adjacent vertebrae includes the step of extending the second articulated fastener from a junction of a superior articular process and a transverse process of a superior vertebra, in an inferior direction through a centrum of the superior vertebra, obliquely traversing a pedicle, through an inferior endplate of the superior vertebra, through an interbody space, and into a vertebral body of an inferior vertebra.

5. The method of claim 1, wherein the step of inserting the first articulated fastener into a plurality of adjacent vertebrae includes the step of extending the first articulated fastener from a lateral junction of a pedicle and a transverse process of an inferior vertebra, diagonally traversing the pedicle, through a superior endplate of the inferior vertebra, across an interbody space, through an inferior endplate of a superior vertebra, through a centrum of the superior vertebra, and to a junction of a superior endplate of the superior vertebra with an anterior vertebral surface; and
the step of inserting the second articulated fastener into a plurality of adjacent vertebrae includes the step of extending the second articulated fastener from a lateral junction of a pedicle and a transverse process of an inferior vertebra, diagonally traversing the pedicle, through a superior endplate of the inferior vertebra, across an interbody space, through an inferior endplate of a superior vertebra, through a centrum of the superior vertebra, and to a junction of a superior endplate of the superior vertebra with an anterior vertebral surface.

6. The method of claim 1, wherein the step of inserting the first articulated fastener into a plurality of adjacent vertebrae includes the step of extending the first articulated fastener toward a midline of at least one of the first and second vertebrae, and the step of inserting the second articulated fastener into a plurality of adjacent vertebrae includes the step of extending the second articulated fastener toward a midline of at least one of the first and second vertebrae.

7. The method of claim 1, including the step of expanding an expanding portion laterally from at least one of the first and second articulating portions to at least partially occupy an interbody space between the vertebrae.

* * * * *